United States Patent [19]

Sache

[11] 4,055,648
[45] Oct. 25, 1977

[54] PAPAVERINE THIENYL-CARBOXYLATES AND MEDICAMENTS CONTAINING THEM

[75] Inventor: Edgar Sache, Bures-sur-Yvette, France

[73] Assignee: Choay S.A., Paris, France

[21] Appl. No.: 541,279

[22] Filed: Jan. 15, 1975

[30] Foreign Application Priority Data

Jan. 16, 1974 France .............................. 74.01460

[51] Int. Cl.$^2$ .................. A61K 31/485; C07D 217/20
[52] U.S. Cl. ...................................... 424/260; 260/285
[58] Field of Search ........................... 260/286 C, 285; 424/258, 260

[56] References Cited

U.S. PATENT DOCUMENTS

| 2,027,722 | 1/1936 | Diehl ................................... 424/260 |
| 2,507,086 | 5/1950 | Baizer .................................. 260/285 |
| 3,823,234 | 7/1974 | Mauvernay ........................ 424/260 |

*Primary Examiner*—Paul M. Coughlan, Jr.
*Attorney, Agent, or Firm*—Weiser, Stapler & Spivak

[57] ABSTRACT

Novel salts of papaverine are constituted by the thienyl-carboxylates of papaverine notably papaverine thienyl-2-carboxylate. A papaverine thienyl-carboxylate is prepared by reacting papaverine base with the corresponding thiophene carboxylic acid. The medicaments comprise, as active principle, a papaverine thienyl-carboxylate associated with a solid excipient making it suitable for administration by the oral route, or with an excipient making it suitable for administration by the rectal route. The medicament, is useful for the treatment of hyperspasmodicity of the smooth muscles, and for the treatment of vascular disorders, notably due to senescence, more particularly those bringing into action cortical reactivity.

18 Claims, No Drawings

PAPAVERINE THIENYL-CARBOXYLATES AND MEDICAMENTS CONTAINING THEM

The invention relates to new salts of papaverine and to medicaments containing them. It relates also to a process for the preparation of these salts.

Papaverine, mostly used in the form of the hydrochloride of papeverine base, is a well-known active principle of medicines, notably for its aptitude to correct hyperspasmodicity conditions of the smooth muscles and for its effect on platelet adhesivity. The administration of papaverine in repeated doses may however induce secondary effects making its use delicate (somnolence, constipation, increased excitability of the reflexes and digestive disorders).

It is an object of the invention to provide new salts of papaverine having papaverine activity associated with papaverine base, distinctly more intense than the salts of papaverine which have been in current use until now in therapeutics.

It is another object to provide medicaments having, for equal therapeutic activity, a lower content of papaverine than medicaments used until now.

It is a further object to provide an improved method of treating smooth muscle and vascular disorders.

The new products according to the invention are constituted by papaverine thienyl-carboxylates.

The process according to the invention is characterised in that papaverine base is reacted with the corresponding thienyl-carboxylic acid.

The thienyl-carboxylates of papaverine, and more particularly papaverine thienyl-2-carboxylate, have a papaverinic activity, associated with the papaverine base, distinctly higher than the salts of papaverine used until now, notably in that they have a more intense effect on platelet adhesivity on the one hand, and on disturbances of the oxygen metabolism and of glucose metabolism at the level of the brain such as for example in cerebral oedema on the other hand. These enhanced properties are all the more unexpected since the corresponding thienyl-carboxylic acids are themselves devoid of this type of activity.

Other objects, features and advantages of the invention will appear also in the course of description which follows of examples of papaverine thienyl-carboxylates, of their methods of preparation and their physicochemical and pharmacological properties.

EXAMPLE 1

Preparation of papaverine thienyl-2-carboxylate of the formula:

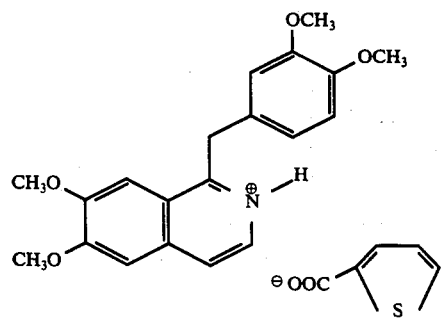

5.02 g of papaverine base is dissolved in 250 ml of methanol kept in warm condition. To this solution 1.90 g of thienyl-2-carboxylic acid is added and it is stirred for one hour. The methanol is evaporated under reduced pressure and the residue is left to crystallize (overnight); this residue is recrystallized in absolute alcohol. There is obtained, with a yield of 90–93%, a papaverine thienyl-2-carboxylate having the following analytical characteristics:

| Empirical Formula: | $C_{25}H_{25}NO_6S$ | | |
|---|---|---|---|
| Analysis: | C | H | N |
| Calculated %: | 64.22 | 5.39 | 3.00 |
| Found %: | 64.41 | 5.57 | 3.20 |
| MW: 467,53: | | | |
| m.p.: 147° C. | | | |
| Soluble in methanol | | | |
| Soluble in warm ethanol. | | | |

EXAMPLE 2

Preparation of papaverine thienyl-carboxylate of the formula:

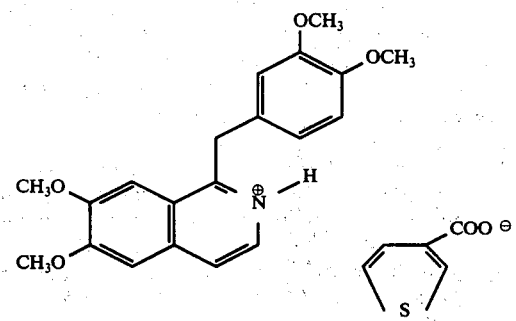

Procedure is as under the conditions described in Example 1, but replacing the thienyl-2-carboxylic acid with thienyl-3-carboxylic acid.

Papaverine thienyl-3-carboxylate is obtained having the following analytical characteristics.

| Empirical Formula: | $C_{25}H_{25}NO_6S$ | | |
|---|---|---|---|
| Analysis: | C | H | N |
| Calculated %: | 64.22 | 5.39 | 3.00 |
| Found %: | 64.10 | 5.30 | 3.04 |
| MW: 467,53 | | | |
| m.p.: 157° C. | | | |
| Soluble in methanol | | | |
| Soluble in hot ethanol | | | |

The papaverine thienyl-3-carboxylate is in the form of white crystals.

It can form solutions in water containing up to 1% of product and solutions in dimethylsulfoxide (DMSO) containing notably from 5 to 10% by weight of product.

Pharmacological Properties of the Thienyl-Carboxylates of Papaverine

1. Study of the Action in Vitro and in Vivo of Thienyl-2-Carboxylate of Papaverine on Platelet Adhesivity The technique used is that described in the study "Disseminated and localized intravascular coagulations" of C. Raby, Masson et Cie, 1970, p. 91–93.

The parameter used in this technique is the level of platelet adhesivity. The blood to be tested is run through a column of glass beads. Platelet counts are carried out on the blood before and after passage respectively through the glass beads. The difference between these two counts enables the level of platelet adhesivity to be estimated. Comparison of the adhesivity ratios, measured in the treated animals and in the controlled animals, enables the effect of the product under test to be estimated.

In in vitro test the levels of platelet adhesivity measured on control specimens of blood and on blood specimens to which have previously been added doses of the product under test, are compared.

In the in vivo test the animal to be tested (the rabbit) is injected with thrombin (20 U) by the intravenous route, for the purpose of sensitizing the platelets, and the product under study is then injected. The behavior of the platelets is studied by samples taken before and after administration of the product under study.

Papaverine thienyl-2-carboxylate has, in all these tests, been applied in the dissolved state in a 1 % aqueous solution of methanol in isotonic chloride solution, in the proportion of 13 mg of papaverine thienyl-2-carboxylate per 100 ml of this solution.

In the in vitro tests, it was observed that a dose of papaverine thienyl-2-carboxylate of 2.88 $\gamma$/ml of blood (namely the equivalent of 2.10 $\gamma$/ml of papaverine base) had an activity equivalent to that of a dose of 80 $\gamma$/ml of papaverine citrate (namely the equivalent of 51.2 $\gamma$/ml papaverine base) and of a dose of 50 $\gamma$/ml of papaverine hydrochloride (namely the equivalent of 45 $\gamma$/ml of papaverine base).

These results show that, in this test, papaverine thienyl-carboxylate has an activity considerably greater than that of the known salts of papaverine used (at equal doses expressed in terms of papaverine base). These results are all the more unexpected since, in the same test, thiophene carboxylic acid, at doses of 8 and 16 $\gamma$/ml respectively, is completely inactive.

30 Animals were treated in the in vivo tests:
10 animals with the thrombin alone (control animals),
10 animals with the thrombin and papaverine citrate, at the dose of 32 $\gamma$/ml, namely the equivalent of 20 $\gamma$/ml of papaverine base,
10 animals with thrombin and 2.88 $\gamma$/ml of papaverine thienyl-2-carboxylate, namely the equivalent of 2.10 $\gamma$/ml of papaverine base.

At these doses, papaverine citrate is shown to be inactive, whilst papaverine thienyl-2-carboxylate is shown to act favourably on the adhesivity rate of the platelets.

2. Effect on Disturbances of the Oxygen Metabolism and of the Glucose Metabolism at the Level of the Brain: on Disturbances of Cerebral Electrogenesis, Caused in the Rabbit by Unilateral Cerebral Oedema In the rabbit a cerebral oedema is caused, which has the effect of disturbing the irrigation of the cerebral vessels, hence reducing the amounts of oxygen and of glucose brought thereto. The effect of a medicament on the oxygen and glucose metabolisms is estimated, in this test, by the reduction in the deleterious effects of oedema on certain parameters with respect to the controls.

The technique used is that described in the work "Aggressology" 1972, 13, Vol. IV, p. 257–259 (M.G. Borzex, M. Labos, J. Cahn). The principle of the test consists of producing unilateral ablation of a bone flap of 7 to 10 mm diameter in the occipital region. The incision, 48 hours later, of the dura mater or dural (membrane which surrounds the brain) results in the formation of an oedema.

Two essential parameters are selected to judge the seriousness of the oedematous effect and to subsequently permit estimation of the effects of the compound under study: electrogenesis on the "injured" hemisphere and the development of residual cortical reactivity in this same hemisphere.

The electrogenesis is judged by variations in the index (R), defined as the ratio of the number of rapid rhythms (theta arousal rhythm) to the number of slow waves of the electrocorticogram (determined by electroencephalography). On the injured side, the size of the slow waves tends to increase and that of the thetarhythm connected with the arousal response to be eliminated. The oedema hence induces a reduction in the "R" index.

The residual cortical reactivity of the hemisphere carrying the cerebral oedema expresses the percentage of reactivity which persists with regard to a sensorial stimulation (auditive stimulation or nociceptive stimulation of the cutanous nerve ends by pinching of the dorsal skin) despite the oedematous degradation.

An active medicament tends to increase the value of the "R" index and to reestablish the residual cortical reactivity of the animals which have undergone the operation. The activities of the medicament expressed in % growth for the index R, and in % growth for the residual cortical reactivity, are compared with results observed in the controls.

The study was carried out on 42 male rabbits, active, of average weight 2.5 kg (and in eight control animals). The product to be tested (papaverine thienyl-2-carboxylate) was administered by the intraduodenal route, 42 hours after ablation of the bone flap and just before the incision of the dural. This route of administration was selected since it is equivalent to the administration by the oral route.

The rabbits studied were divided in the following manner:
a series of eight "control" animals receiving 2 ml/kg of isotonic chloride solution;
three series of eight rabbits, each having received respectively 5, 10 and 20 mg/kg of papaverine hydrochloride;
two series of eight animals, each receiving respectively 6.2 and 12.4 mg/kg of papaverine thienyl-2-carboxylate (dissolved in alcoholized water, containing 1 ml of alcohol per 30 ml of water);
lastly, two rabbits receiving 2 mg/kg of papaverine hydrochloride dissolved in alcoholized water.

The doses of 5 and 10 mg/kg of papaverine hydrochloride correspond respectively to doses of 6.2 and 12.4 mg/kg of papaverine thienyl-2-carboxylate, if reduced to the corresponding doses of papaverine-base (respectively 4.51 and 9.02 mg/kg).

The development of the two above indicated parameters (expressed below in average values) is observed for 30 hours following the incision of the dural.

The dose of 5 mg/kg of papaverine hydrochloride shows itself to be practically inactive.

At a dose of 10 mg/kg of papaverine hydrochloride, a biological effect is obtained in about 50% of the treated animals. The rise in the "R" index established in the eight animals is thus 19% during the first 4hours, this rise changing and falling to 14% between 4 and 6 hours. The residual cortical reactivity is only improved in the course of the 2 hours which follow administration in four rabbits out of eight (average 29% in the eight rabbits).

At a dose of 20 mg/kg of papaverine hydrochloride, the effects are very distinct. The average rise in the "R" ratio is about 40 to 45% and stabilises at this value for the first 6 hours; this action affects six animals in eight.

The residual cortical reactivity is improved in the same proportion during 4 hours, this percentage changing but being still about 23% between 4 and 6 hours.

As regards papaverine thienyl-2-carboxylate, there is already observed at the dose of 6.2 mg/kg a very distinct improvement of the two parameters in five rabbits out of eight for at least 4 hours, with a slight predominance for the residual cortical reactivity. The extension in the duration of the arousal reactions on the "injured" hemisphere is on the average, in the eight rabbits, 45.4% between the second and the fourth hours. The average variation in the eight rabbits of cortical electrogenesis is comprised between 24 and 28%.

At the dose of 12.4 mg/kg, a distinct rise in the "R" index is observed (on the average 38.5%). The effect on the residual cortical reactivity is particularly distinct since during the maximum effect, situated between 2 and 4 hours, the average improvement, in the eight rabbits, is equal to 54.2%, this value remaining substantially stable during the first 6 hours. The effect is particularly distinct in seven rabbits out of eight.

The collected results obtained in the course of this study by the intraduodenal route show, in the tests concerned, that papaverine thienyl-2-carboxylate is distinctly more active than papaverine hydrochloride.

At the dose of 6.2 mg/kg, papaverine thienyl-carboxylate is active, whilst the equivalent dose of papaverine hydrochloride is practically ineffective. At the dose of 6.2 mg/kg, papaverine thienyl-2-carboxylate exerts a favorable effect rather similar to that exerted by a dose of 20 mg/kg of papaverine hydrochloride (which dose is multiplied by four when it is reduced to papaverine-base).

The dose 12.4 mg/kg of papaverine thienyl-carboxylate exerts a slightly more intense effect and more prolonged than a dose twice as great of papaverine hydrochloride (20 mg/kg).

Moreover, the much more marked activity of papaverine thienyl-2-carboxylate with respect to the residual cortical reactivity induces also a particularly interesting difference in the nature of the therapeutic effects of the thienyl-2-carboxylate and the hydrochloride respectively of papaverine. In therapeutic treatments directed to permitting cerebral function recovery, notably at the level of the metabolisms of oxygen and of glucose, the use of papaverine thienyl-2-carboxylate is more indicated than that of the hydrochloride, even if the differences in doses which have been discussed above are not taken into account.

3. Study of the $LD_{50}$ in the Mouse

Study of the $LD_{50}$ (by the oral route) in the mouse has established the complete inoccuousness of papaverine thienyl-carboxylates. Thus, the $LD_{50}$ of papaverine thienyl-2-carboxylate is 1,300 mg/kg of mouse (deviations between 1,035 mg/kg and 1,632 mg/kg in 48 hours for $P = 0.005$).

It results from the foregoing that papaverine thienyl-carboxylates show, when introduced into the digestive tract, the properties of the salts of papaverine normally used in therapeutics, but especially for papaverine thienyl-2-carboxylate—to a much higher degree: the conventional vasomotor effect used to correct hyperplasmodicity conditions of the smooth muscles; effect on platelet adhesivity and on disturbances of electrogenesis at the level of the brain. In addition the properties, notably of papaverine thienyl-2-carboxylate, are qualitatively distinguished from those of the above mentioned known salts of papaverine, particularly at the level of the effect on cortical reactivity.

In all cases, the papaverine thienyl-carboxylates give, comparatively with the conventional salts of papaverine, for lower doses expressed as papaverine base, notably superior results, characterized by the intensity and duration of action; as regards more particularly activity on the cortical reactivity, which reflects the normal basic cerebral physiological activity, the conventional salts of papaverine have a fleeting and irregular effect, whilst the salts according to the invention give for the same doses expressed as papaverine base constant results which are more intense and of longer duration.

In general, the new salts are indicated in the following cases:

Hyperspasmodicity of the smooth muscles, more particularly:
of the peripheral vascular system (peripheral arterial system) or central vascular system,
of the cerebral, cardiac, pulmonary, occular systems,
of the visceral system (digestive tract, hepato-biliary tract, urinary tract, female genital tract).
Disorders of platelet adhesivity.
Disturbances of cerebral electrogenesis resulting from vascular disorders, notably due to senescence.

The medicaments according to the invention are preferably administered by the oral or rectal route. Advantageously recourse is had to solid pharmaceutical forms (pills, gelules, tablets) for oral administration, suppositories for administration by the rectal route.

The salts according to the invention may be associated with any pharmaceutically acceptable excipients, compatible with the mode of administration: preferably solid vehicles for the oral forms, of the type of glycerides or the like for rectal forms.

The active principles according to the invention lend themselves to the production of "time delay" medicaments using suitable excipients for this type of administration.

By way of indication, the doses to be used in man are normally situated between 125 and 750 mg per day, divided into two to six administrations (namely 90 to 500 mg of papaverine-base per day). The medicaments according to the invention may also be used in veterinary medicines for the treatment of similar disorders in animals.

As is self-evident, the invention relates also to the products which only constitute equivalents of papaverine thienyl-carboxylates, more particularly papaverine thienyl-2-carboxylate, notably those which are obtained by modifications of the molecule having no other purpose than that of preserving in these equivalent products the essential properties which have been described of papaverine thienyl-carboxylates, notably at the level of cortical reactivity.

I claim:

1. The papaverine compounds selected from the group consisting of: papaverine thienyl-2-carboxylate and papaverine thienyl-3-carboxylate.
2. Papaverine thienyl-2-carboxylate.
3. Papaverine thienyl-3-carboxylate.
4. Medicament comprising, a pharmaceutically acceptable carrier and as active principle in a therapeutically effective amount, for the treatment of hyperspasmodicity of smooth muscles and vascular disorders, a papaverine thienyl-carboxylate according to claim 1.

5. Medicament according to claim 4, wherein the papaverine thienyl-carboxylate is associated with a solid excipient making it suitable for oral administration.

6. Medicament according to claim 4, wherein the papaverine thienyl-carboxylate is associated with an excipient making it suitable for rectal administration.

7. Method for the treatment of hyperspasmodicity of the smooth muscles, in a non-human animal, comprising administering to the animal a medicament, according to claim 4.

8. Method for the treatment of vascular disorders and promoting cortical reactivity, in a non-human animal, comprising administering to the animal, a medicament, according to claim 4.

9. Method for treating hyperspasmodicity of the smooth muscles or disorders of platelet adhesivity or disturbance of cerebral electrogenesis resulting from vascular disorders comprising administering an effective amount of a thienyl-carboxylate of papaverine according to claim 1.

10. Method of treatment according to claim 9, wherein said thienyl-carboxylate of papaverine is administered at the rate of about 125 to 750 mg per daily dose.

11. A pharmaceutical composition comprising the papaverine of claim 2 in a therapeutically effective amount, for the treatment of hyperspasmodicity of smooth muscles and vascular disorders, and a pharmaceutically acceptable carrier.

12. The method of treatment of vascular disorders which comprises administering the composition of claim 11 to the subject in a daily dosage of about 90 to 500mg of the papaverine (calculated on the basis of the base).

13. The solid pharmaceutical composition of claim 11.

14. The solution of the product of claim 2 which is an isotonic chloride solution containing 1% methanol having the proportion of 13mg of papaverine thienyl-2-carboxylate per 100 ml of solution.

15. The method of claim 9 wherein the administration is for control of hyperspasmodicity of the smooth muscles.

16. The method of claim 9 wherein the administration is for control of disorders of platelet adhesivity.

17. The method of claim 9 wherein the administration is for control of cerebral electrogenesis caused by vascular disorders.

18. The method of claim 17 wherein the administration is for control of cerebral electrogenesis by senescence.

* * * * *